United States Patent
Woodward

(10) Patent No.: US 9,896,463 B2
(45) Date of Patent: Feb. 20, 2018

(54) PREPARATION OF PURIFIED PHOSPHORODIAMIDITE

(71) Applicant: RHODIA OPERATIONS, Paris (FR)

(72) Inventor: Gary Woodward, Cheshire (GB)

(73) Assignee: Rhodia Operations, Paris (FR)

( * ) Notice: Subject to any disclaimer, the term of this patent is extended or adjusted under 35 U.S.C. 154(b) by 0 days.

(21) Appl. No.: 15/110,971

(22) PCT Filed: Jan. 15, 2015

(86) PCT No.: PCT/EP2015/050669
§ 371 (c)(1),
(2) Date: Jul. 12, 2016

(87) PCT Pub. No.: WO2015/107110
PCT Pub. Date: Jul. 23, 2015

(65) Prior Publication Data
US 2016/0333034 A1    Nov. 17, 2016

Related U.S. Application Data

(60) Provisional application No. 61/927,517, filed on Jan. 15, 2014.

(51) Int. Cl.
*C07F 9/02* (2006.01)
*C07F 9/24* (2006.01)

(52) U.S. Cl.
CPC .......... *C07F 9/2412* (2013.01); *C07F 9/2408* (2013.01); *C07F 9/2458* (2013.01)

(58) Field of Classification Search
CPC ................................ C07F 9/02; C07F 9/2412
See application file for complete search history.

(56) References Cited

U.S. PATENT DOCUMENTS 7,276,620 B2 * 10/2007 Harris ................ C07H 21/00
558/192

FOREIGN PATENT DOCUMENTS

WO    2004058779 A1    7/2004

OTHER PUBLICATIONS

Armarego et al., "Chemical Methods Used in Purification", Jan. 1, 2003, Purification of Laboratory Chemicals, 5th Edition.

* cited by examiner

Primary Examiner — Golam M M Shameem

(57) ABSTRACT

The instant invention relates to a method of phosphorodiamidite production that comprises: (E1) preparing a purified solution of a dialkylamine in a polar solvent as follows: —the dialkylamine dissolved in a polar solvent is contacted with a quantity of phosphorus trihalide that is sufficient to react with the alcohol impurities contained in the dialkylamine but sufficiently low to leave a major part of the dialkylamine unreacted, whereby a mixture is obtained that contains the dialkylamine in the polar solvent and reaction products of the impurities with the phosphorous trihalide; —the unreacted dialkylamine and polar solvent present in the mixture obtained in step (E1.1.) are extracted from the solution S by their difference of volatility, typically by distillation, whereby the purified solution of the dialkylamine in the polar solvent is obtained; (E2) the purified solution of dialkylamine in a polar solvent as obtained in step (E1) is reacted with a phosphorus trihalide, whereby an intermediate compound is formed; (E3) the intermediate compound obtained in step (E2) is reacted with a hydroxyalkyl compound in the presence of a non-polar co-solvent.

13 Claims, No Drawings

PREPARATION OF PURIFIED PHOSPHORODIAMIDITE

This application is a U.S. national phase entry under 35 U.S.C. § 371 of International Application No. PCT/EP2015/050669, filed on Jan. 15, 2015, which claims priority to U.S. Provisional Application No. 61/927,517, filed Jan. 15, 2014. The entire contents of these applications are incorporated herein by this reference.

The present invention relates to an improved method for the production of phosphorodiamidites, that allow to obtain phosphorodiamidites that may especially be used in the pharmaceutical and biotechnology industry.

Phosphorodiamidites are well known compounds, that are in particular used as intermediates in the pharmaceutical and biotechnology industry, e.g. in the manufacture of antineoplastic agents.

However, to be suitable for use in such industries, phosphorodiamidites must be of high purity (typically of at least 99% by 31P NMR). This is especially significant for 2-Cyanoethyl N,N,N',N'-tetraisopropylphosphorodiamidite of formula (NC—$C_2H_4$—O—P—($—NiPr_2)_2$, which is a commercially important intermediate in the synthesis of oligonucleotides.

A method for obtaining phosphorodiamidites having a relatively high purity has been disclosed in WO 2004/058779, said method comprising (1) reacting a phosphorus trihalide with a dialkyl amine in a polar solvent to form an intermediate compound and (2) subsequently reacting the intermediate compound with a hydroxyalkyl compound and a dialkyl amine, in the presence of a non-polar co-solvent, which leads to:
- a precipitation of the salt produced in the first step E1 (iPr2NH2+Cl− in the case of 2-Cyanoethyl N,N,N',N'-tetraisopropylphosphorodiamidite); and
- a reaction of the intermediate compound with an hydroxyl compound, typically cyanoethanol, in the presence of a non-polar co-solvent, which produces:
  - a salt (iPr2NH2+Cl− in the case of 2-Cyanoethyl N,N,N',N'-tetraisopropylphosphorodiamidite), that precipitates.
  - the sought phosphorodiamidite (2-Cyanoethyl N,N,N',N'-tetraisopropylphosphorodiamidite, for example) obtained in solution, separated from the solid, having a relatively high purity, typically of at least 96%.

One aim of the instant invention is to provide a method that allow to obtain phosphorodiamidites of higher purity.

To this end, the invention proposes to make use of the method of WO 2004/058779, but with a preliminary step of purification of the reactants, that especially allows to eliminate alcohol impurities present in the diallkylamine (for example the isopropanol impurities that are present in diisopropylamine, in the case of the preparation of 2-Cyanoethyl N,N,N',N'-tetraisopropylphosphorodiamidite).

More precisely, according to a first aspect, one subject-matter of the instant invention is a method for preparing a phosphorodiamidite, from a dialkylamine containing impurities including at least an alcohol, that comprises the following steps:
- (E1) a purified solution of the dialkyl amine in a polar solvent is prepared as follows:
  - (E1.1.) the dialkylamine dissolved in a polar solvent is contacted with a quantity of phosphorus trihalide that is sufficient to react with the alcohol impurities contained in the dialkylamine, and optionally with other impurities contained in the dialkylamine or in the polar solvent, but sufficiently low to leave a major part of the dialkylamine unreacted, whereby a mixture is obtained that contains the dialkylamine in the polar solvent and reaction products of the impurities with the phosphorous trihalide;
  - (E1.2.) the unreacted dialkylamine and polar solvent present in the mixture obtained in step (E1.1.) are extracted from the solution S by their difference of volatility, typically by distillation, whereby the purified solution of the dialkyl amine in the polar solvent is obtained;
- (E2) the purified solution of dialkyl amine in a polar solvent as obtained in step (E1) is reacted with a phosphorus trihalide, whereby an intermediate compound is formed;
- (E3) the intermediate compound obtained in step (E2) is reacted with a hydroxyalkyl compound in the presence of a non-polar co-solvent, optionally together with a suitable amine base.

In the scope of the instant invention, the inventors have now made evident that the above step (E1) inhibits the formation of by-products in steps (E2) and (E3) that are otherwise extremely difficult to eliminate after the reactions of step (E2) and (E3).

As a consequence, the process of the invention allows to obtain purified phosphorodiamidite that cannot be obtained according to another method. According to another specific aspect, a subject-matter of the instant invention is the highly purified phosphorodiamidites as obtained by the process of the invention.

Especially, starting from diisoproylamine comprising isopropanol as an impurity, the process of the instant invention allows to obtain purified 2-Cyanoethyl N,N,N',N'-tetraisopropylphosphorodiamidite that is free from iPr—O—P—(N-iPr$_2$)$_2$ impurity.

The use of steps (E1), (E2) and (E3) according to the invention may further allows a reduction of other side products linked to the presence of other impurities than alcohol in the reactants. Step (E1) actually leads to a reduction of the content of impurities that my react with the phosphorus trihalide. Especially, step (E1) allows to reduce the content of usual impurities present in dialkyl amines, including for example isomers of the used dialkyl amine. For example, in the specific case if diisopropyl amine, step (E1) eliminates all or part N-ethyl, N-isopropylamine and N-(1-propyl), N-isopropyl amine that are commonly present as impurities.

Whatever the exact nature of the reactants used in step (E&), (E2) and (E3) and of the impurities that they contain, the phosphorus trihalide used according to the instant invention is preferably phosphorus trichloride PCl$_3$. Alternatively, the phosphorus trihalide used according to the instant invention may also be phosphorus tribromide PBr$_3$. Generally (but not necessarily), the phosphorus trihalide used in step (E1) and the phosphorus trihalide used in step (E2) are the same (typically PCl$_3$ in the to steps).

The dialkyl amine used according to the invention is preferably diisopropylamine, e.g. containing isopropanol as an impurity (typically the used diisopropylamine contains isopropanol and N-ethyl, N-isopropyl amine and N-(1-propyl), N-isopropyl amine as impurities). In that case, the prepared phosphorodiamidite is typically 2-Cyanoethyl N,N,N',N'-tetraisopropylphosphorodiamidite.

Alternatively the dialkyl amine may be dimethylamine, diethylamine, di-n-propylamine, di-n-butylamine, di-isobutylamine or di-tert-butylamine.

Whatever its nature, the dialkyl amine used according to the invention may include various proportion of impurities (especially at least one alcohol and optionally other impurities). The process of the invention allows use of any alkylamine, whatever the content of impurities. Depending on this content, only one parameter has to be adapted, namely the quantity of phosphorus trihalide to be used in step (E1), that should be sufficiently small to let a major part of the dialkyl amine unreacted (by "major part", it should be understood that preferably at least 75%, more preferably at least 90%, and even more preferably at least 95% of the dialkylamine is let unreacted in step E1—this is however preferable for economical reason only, and the high purity may be obtained for lower content of unreacted dialkylamine).

The polar solvent used according to the invention is preferably a nitrile compound, in particular, acetonitrile. Alternatively the polar solvent may be propionitrile or benzonitrile.

The hydroxyalkyl compound is preferably hydroxypropionitrile. Alternatively the hydroxyalkyl compound may be methanol, tert-butyl alcohol or other suitable hydroxyalkyl compounds which are known to be suitable for the manufacture of phosphorodiamidites.

The alkane co-solvent is preferably heptane or hexane. Other suitable $C_5$ to $C_9$ aliphatic hydrocarbons include pentane. Suitable alicyclic hydrocarbons include, for example, cyclohexane.

The ratio of polar solvent to non-polar solvent may typically be from 5:1 to 1:5 and is generally around 1:1 (for example from 2:1 to 1:2).

The process of the invention is typically carried out in dry conditions and under inert atmosphere.

The method according to the invention provides a phosphorodiamidite compound according to Formula I:

$$(R_2N)_2-P-O(CH_2)_n-CN \quad (I)$$

wherein R is a $C_1$ to $C_4$ alkyl, hydroxyalkyl or oxyalkyl group; and n is a whole number of from 1 to 4.

The compound according to formula I is preferably 2-cyanoethyl tetraisopropyl phosphorodiamidite wherein R is isopropyl, and n=2.

The present invention also provides the use of a compound of formula I in the synthesis of oligonucleotides.

The invention will now be illustrated by the following examples.

EXAMPLES

The process of the invention has been carried out in the following conditions, in a clean and dried apparatus maintained under inert atmosphere.

Example 1

First Step:
PCl$_3$ (8.09 g; 0.0589 moles) was added slowly to a mixture of MeCN (200 g) and diisopropylamine (DIPA) (120.84 g; 1.194 moles). The resultant mixture was stirred for 5 hours. The reaction mixture obtained was then vacuum distilled, whereby a purified DIPA/MeCN solution was obtained (163.97 g, namely 41 wt % DIPA determined by 1H NMR).
Second Step:
PCl3 (15.07 g; 0.110 moles) was added slowly to the purified DIPA/MeCN solution obtained in the first step (95.89 g MeCN/66.63 g DIPA, 0.658 moles). The reaction mixture was left stirring overnight.
Third Step:
Heptane (110 g) was added to the reaction mixture obtained in the second step and then cyanoethanol (7.64 g, 0.107 moles) was added slowly.
Recovery of the Phosphorodiamidite
Solid by-products of the reaction were removed by filtration and the filtrate was then washed (1 H$_2$O wash and then 2 MeCN/H2 washes and then a final MeCN wash).
Heptane was removed under vacuum to give the crude product as a clear colourless liquid.

Example 2

First Step:
PCl3 (8.47 g; 0.0617 moles) was added slowly to a mixture of MeCN (200 g) and DIPA (122.16 g; 1.207 moles). The resultant mixture was stirred for 5 hours. The reaction mixture obtained was then vacuum distilled, whereby a purified DIPA/MeCN solution was obtained (215.06 g, namely 41 wt % DIPA determined by 1H NMR).
Second Step:
PCl3 (14.81 g; 0.108 moles) was added slowly to the purified DIPA/MeCN solution obtained in the first step (94.25 g MeCN/65.50 g DIPA, 0.658 moles). The reaction mixture was left stirring overnight.
Third Step:
Heptane (107 g) was then added to the reaction mixture and then cyanoethanol (7.60 g, 0.107 moles) was added slowly.
Recovery of the Phosphorodiamidite
Solid by-products of the reaction were removed by filtration and the filtrate was then washed (1 H2O wash and then 2 MeCN/H2O washes and then a final MeCN wash).
Heptane was removed under vacuum to give the crude product as a clear colourless liquid.

COMPARATIVE DATA

For seek of comparison, a control has been made, wherein second and third steps of Example 1 have been carried out, without the purification of the first steps.

The Table 1 below reports the effect of the purification steps on the impurities content in the final products, and shows a clear decrease.

Three impurities have been analyzed, namely:
the impurity due to isopropanol ("isopropyl impurity");
the impurity due to N-ethyl, N-isopropyl amine ("ethyl isopropyl impurity")
the impurity due to N-(1-propyl), N-isopropyl amine ("isopropyl propyl impurity)

The Table 1 reports the area percentage from $^{31}$P NMR analysis of the phosphorodiamidite and of the three impurities, that shows that the purification step:
eliminates the isopropyl impurity
substantially reduce (by 90%) the two other impurities

TABLE 1

| Composition of the final product ($^{31}$P NMR) | | | |
|---|---|---|---|
| phosphorodiamidite | isopropyl impurity | Ethyl isopropyl impurity | Isopropyl propyl impurity |
| Control | 98.571% | 0.010% | 0.208% | 0.102 |
| Example 1 | 99.541% | Not detected | 0.026% | 0.010% |
| Example 2 | 99.614% | Not detected | 0.026% | 0.011% |

The invention claimed is:

1. A method of phosphorodiamidite production, the method comprising:
   (E1) preparing a purified solution of a dialkyl amine in a polar solvent as follows:
      (E1.1.) the dialkylamine dissolved in a polar solvent is contacted with a quantity of phosphorus trihalide that is sufficient to react with the alcohol impurities contained in the dialkylamine, and optionally with other impurities contained in the dialkylamine or in the polar solvent, but sufficiently low to leave a major part of the dialkylamine unreacted, whereby a mixture is obtained that contains the dialkylamine in the polar solvent and reaction products of the impurities with the phosphorus trihalide;
      (E1.2.) the unreacted dialkylamine and polar solvent present in the mixture obtained in step (E1.1.) are extracted from the solution S by their difference of volatility whereby the purified solution of the dialkyl amine in the polar solvent is obtained;
   (E2) reacting the purified solution of dialkyl amine in a polar solvent as obtained in step (E1) with a phosphorus trihalide whereby an intermediate compound is formed;
   (E3) reacting the intermediate compound obtained in step (E2) with a hydroxyalkyl compound in the presence of a non-polar co-solvent.

2. The method of claim 1, wherein the dialkyl amine is a diisopropylamine comprising isopropanol as an impurity.

3. The method of claim 2, wherein the dialkyl amine furthermore contains N-ethyl, N-isopropyl amine and N-(1-propyl), N-isopropyl amine as impurities.

4. The method of claim 2, wherein the prepared phosphorodiamidite is 2-Cyanoethyl N,N,N',N'-tetraisopropyl-phosphorodiamidite.

5. The method of claim 1, wherein the phosphorus trihalide is phosphorus trichloride.

6. The method of claim 1, wherein the polar solvent is a nitrile compound.

7. The method of claim 6, wherein the nitrile compound is acetonitrile.

8. The method of claim 6, wherein the polar solvent is propionitrile or benzonitrile.

9. The method of claim 1 wherein the hydroxyalkyl compound is hydroxypropionitrile.

10. The method of claim 1 wherein the hydroxyalkyl compound is methanol or tert-butyl alcohol.

11. The method of claim 1 wherein the co-solvent is a $C_5$ to $C_9$ aliphatic hydrocarbon.

12. The method of claim 1 wherein the co-solvent is an alicyclic hydrocarbon.

13. The method of claim 1, wherein the unreacted dialkylamine and polar solvent present in the mixture obtained in step (E1.1.) are extracted from the solution S by distillation.

* * * * *